(12) United States Patent
Baugh et al.

(10) Patent No.: US 6,864,334 B2
(45) Date of Patent: Mar. 8, 2005

(54) MULTI-DENTATE LATE TRANSITION METAL CATALYST COMPLEXES AND POLYMERIZATION METHODS USING THOSE COMPLEXES

(75) Inventors: Lisa Saunders Baugh, Ringoes, NJ (US); Abhimanyu Onkar Patil, Westfield, NJ (US); Donald Norman Schulz, Annandale, NJ (US); Robert Timothy Stibrany, Long Valley, NJ (US); Joseph Anthony Sissano, Leonardo, NJ (US); Stephen Zushma, Clinton, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 0 days.

(21) Appl. No.: 10/893,429

(22) Filed: Jul. 16, 2004

(65) Prior Publication Data

US 2005/0004334 A1 Jan. 6, 2005

Related U.S. Application Data

(62) Division of application No. 09/941,881, filed on Aug. 28, 2001, now Pat. No. 6,809,058.

(51) Int. Cl.$^7$ ............................. C08F 4/44; C08F 4/06
(52) U.S. Cl. ........................................ 526/161; 526/172
(58) Field of Search .................................. 526/161, 172

(56) References Cited

U.S. PATENT DOCUMENTS 6,037,297 A * 3/2000 Stibrany et al. ............ 502/155
6,417,303 B1 * 7/2002 Stibrany et al. ............ 526/161
6,479,425 B1 * 11/2002 Stibrany et al. ............ 502/165

FOREIGN PATENT DOCUMENTS

WO    WO 99/30822    *  6/1999
WO    WO 00/35974    *  6/2000

OTHER PUBLICATIONS

Davis et al., Macromolecules, vol. 33, No. 11, pp. 4039–4047 (2000).*

* cited by examiner

Primary Examiner—Mark L. Bell
Assistant Examiner—J. Pasterczyk
(74) Attorney, Agent, or Firm—Joseph C. Wang

(57) ABSTRACT

The instant invention provides a late transition metal complex which can be used with an activating cocatalyst to produce polymers and copolymers. The invention also provides methods for polymerizing olefins, as well as copolymers having polar monomers incorporated therein. More specifically, the invention provides a composition having the formula $LMXZ_n$, wherein M is selected from the group consisting of Cu, Ag and Au; X is selected from the group consisting of halide, hydride, triflate, acetate, borate, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolate, nitrate, sulfate, nitrile, hydroxide and any other moiety into which a monomer can insert; Z is selected from the group consisting of halide, hydride, triflate, acetate, borate, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolate, carbon monoxide, nitrate, nitrile, hydroxide, sulfate, olefins, water, any other neutral coordinating ligand and any other moiety into which a monomer can insert; n equals 0, 1 or 2; and L is a multi-dentate nitrogen-containing ligand.

28 Claims, No Drawings

MULTI-DENTATE LATE TRANSITION METAL CATALYST COMPLEXES AND POLYMERIZATION METHODS USING THOSE COMPLEXES

This application is a Divisional of U.S. Ser. No. 09/941,881 filed Aug. 28, 2001, now U.S. Pat. No. 6,809,058.

BACKGROUND OF THE INVENTION

1. Field of the Invention

The invention is directed towards multi-dentate late transition metal polymerization catalyst complexes and their use in forming polymers from olefins or polar monomers and copolymers from olefins and polar monomers.

2. Description of the Related Art

Polymers and copolymers may be formed from olefinic monomers by using transition metal catalyst technology. Ziegler-Natta catalysts have been used for many years, while, in more recent years, metallocene catalysts have been preferred in certain applications, since the polyolefins produced via metallocene catalysis often possess superior properties. The most well known metallocene technology employs catalysts containing early transition metal atoms, such as Ti and Zr.

Even though polyolefins formed by such metallocene catalysts possess certain enhanced properties over polyolefins produced by conventional Ziegler-Natta catalysts, further improvements in properties such as wettability and adhesiveness may be possible. It is believed that including polar monomers in an olefinic polymer or copolymer would improve these, and possibly other, properties. Unfortunately, polar monomers tend to poison early transition metal catalysts.

Certain late transition metal complexes, such as those containing palladium and nickel, are more successful in incorporating certain polar monomers into polyolefins. However, most of these catalyst compositions are costly and produce highly branched polymers (e.g., 85–150 branches/1000 carbon atoms). Also, the functionalities are not in the chain, but at the ends of branches. Consequently, they are limited to polar monomer contents of about 15 mol % or less. Another disadvantage of these compositions is that they incorporate only a limited number of polar monomers, such as alkyl acrylates and vinyl ketones.

Recently, novel late transition organometallic catalysts have been made to address the aforementioned problems. More specifically, U.S. Pat. No. 6,037,297 to Stibrany et al., incorporated by reference herein, details group 11 (Cu, Ag and Au; new IUPAC notation) metal-containing catalyst compositions having a pseudotetrahedral geometry that are useful in forming polymers and copolymers having hydrocarbyl polar functionality. Other examples of group 11 metal-containing catalyst compositions are known. See, e.g., WO 98/35996 and JPA 11-171915, both to Shibayama, et al. and both incorporated by reference herein.

However, there is still a need to explore other group 11 metal complexes for use in polymerization processes. Ideally, these late transition metal complexes should be capable of forming olefinic polymers and copolymers containing polar monomers which are not highly branched, have polymer chain functionality and are capable of incorporating a wider variety of polar monomers.

SUMMARY OF THE INVENTION

The instant invention provides a late transition metal complex which can be used with an activating cocatalyst to produce polymers and copolymers. Further, the instant invention can be used to produce polymers and copolymers containing polar monomers. More specifically, the metal complex may be activated by a cocatalyst which is then used to polymerize olefins and copolymerize olefins with polar monomers. Hence, the invention also provides methods for polymerizing olefins, as well as copolymers having polar monomers incorporated therein.

In one embodiment, the invention provides a composition having the formula $LMXZ_n$, wherein M is selected from the group consisting of Cu, Ag and Au; X is selected from the group consisting of halide, hydride, triflate, acetate, borates, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolate, nitrate, sulfate, nitrile, hydroxide and any other moiety into which a monomer can insert; Z is selected from the group consisting of halide, hydride, triflate, acetate, borate, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolate, carbon monoxide, nitrate, nitrile, hydroxide, sulfate, olefins, water, any other neutral coordinating ligand and any other moiety into which a monomer can insert; n equals 0, 1 or 2; and L is a multi-dentate nitrogen-containing ligand.

In another embodiment, the invention is a catalyst composition comprising the reaction product of a metal complex having the formula $LMXZ_n$, as defined above, and an activating cocatalyst. This embodiment of the invention is particularly useful in polymerization chemistry.

In yet another embodiment, the invention provides a method for using the composition to produce polymers and copolymers which contain polar monomer units. The method includes contacting the monomers under polymerization conditions with a catalyst composition comprising a composition having the formula $LMXZ_n$, as defined above, and an activating cocatalyst. Optionally, an oxidizing agent may also be employed during this process.

In a further embodiment, the instant invention provides a novel olefin polymerization process based on the use of a group 11 transition metal complex having the formula $MXZ_n$, as defined above; a multi-dentate nitrogen-containing ligand L; and an activating cocatalyst, which are all contacted with monomers in situ. Unlike Atom Transfer Radical Polymerization (ATRP), the instant invention does not use an alkyl halide initiator, but instead uses a cocatalyst, and can be used to prepare homo- and co-polymers of aliphatic olefins. Further, unlike U.S. Pat. No. 6,037,297, this embodiment of the invention teaches that the use of a preformed metal complex is not a prerequisite. More specifically, it is theorized that the metal complex may be formed in situ by adding the metal compound with a ligand at the same time cocatalyst is added. Hence, the advantages of the instant invention include an in situ method for forming an active catalyst composition which is a step-saving, cost-saving process.

These and other features, aspects and advantages of the present invention will become better understood with regard to the following description and appended claims.

DETAILED DESCRIPTION OF THE INVENTION

The invention relates to a novel metal complex which, when used with an activating cocatalyst, provides a novel catalyst composition. The invention also provides polymerization methods which utilize the catalyst composition. Generally speaking, the methods of the invention produce polymers and copolymers containing polar monomer groups. It should be appreciated by those skilled in the art that use of the general term "copolymers" includes terpolymers and other polymers having various combinations of monomer units.

In one embodiment, the invention comprises a composition comprising the formula $LMXZ_n$, wherein M is selected from the group consisting of Cu, Ag and Au; X is selected from the group consisting of halide, hydride, triflate, acetate, borate, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolate, nitrate, sulfate, nitrile, hydroxide and any other moiety into which a monomer can insert; Z is selected from the group consisting of halide, hydride, triflate, acetate, borate, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolate, carbon monoxide, nitrate, nitrile, hydroxide, sulfate, olefins, water, any other neutral coordinating ligand and any other moiety into which a monomer can insert; n equals 0, 1 or 2; and L is a multi-dentate nitrogen-containing ligand. It should be appreciated by those skilled in the art that the term "multi-dentate" is meant to encompass tri-dentate, tetra-dentate, penta-dentate, hexa-dentate, etc., ligands. More specifically, there will be more than 2 coordinating nitrogen atoms in the ligand.

When the metal composition is reacted with an activating cocatalyst, such as methylaluminoxane ("MAO"), an activated catalyst composition is created. Thus, in another embodiment, the invention is an activated catalyst composition comprising the reaction product of: (a) a metal complex having the formula $LMXZ_n$, wherein M is selected from the group consisting of Cu, Ag and Au; X is selected from the group consisting of halide, hydride, triflate, acetate, borate, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolate, nitrate, sulfate, nitrile, hydroxide and any other moiety into which a monomer can insert; Z is selected from the group consisting of halide, hydride, triflate, acetate, borate, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolate, carbon monoxide, nitrate, nitrile, hydroxide, sulfate, olefins, water, a neutral coordinating ligand, and any other moiety into which a monomer can insert; n equals 0, 1 or 2; and L is a multi-dentate nitrogen-containing ligand; and (b) an activating cocatalyst.

In a preferred embodiment, L is a nitrogen-containing multi-dentate ligand selected from the group consisting of aromatic compounds, aliphatic compounds or a combination of aromatic and aliphatic compounds. The aromatic or aliphatic compounds can be acyclic compounds or they can be connected to form cyclic compounds. Examples of nitrogen-containing aromatic compounds include, but are not limited to, heterocycles, such as a substituted or unsubstituted 2,2':6'2''-terpyridine and a substituted or unsubstituted 2,6-diaryliminopyridine. Each sample heterocycle is shown below.

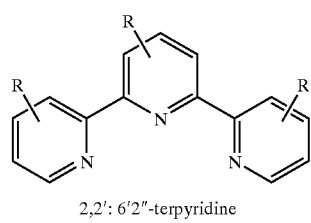

2,2': 6'2''-terpyridine

For the terpyridine structure shown above, R is independently selected from the group consisting of hydrogen, $C_1$ to $C_{20}$ alkyl, $C_4$ to $C_{24}$ cycloalkyl and $C_5$ to $C_{30}$ aromatic groups which, optionally, contain heteroatoms. Although only three R groups are shown, there could be as many as 11 or more R groups, depending upon the size of the aromatic rings.

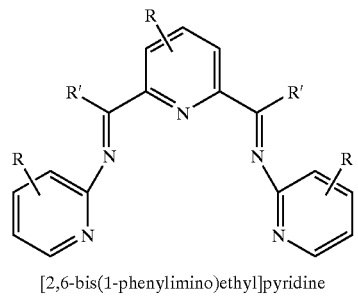

[2,6-bis(1-phenylimino)ethyl]pyridine

For the [2,6-bis(1-phenylimino)ethyl]pyridine structure shown above, R and R' are independently selected from the group consisting of hydrogen, $C_1$ to $C_{20}$ alkyl, $C_4$ to $C_{24}$ cycloalkyl, and $C_5$ to $C_{30}$ aromatic groups which, optionally, contain heteroatoms. Although only three R groups and two R' groups are shown, there could be as many as 15 or more R and R' groups, depending upon the size of aromatic rings.

Similarly, examples of nitrogen-containing aliphatic compounds include, but are not limited to, substituted or unsubstituted diethylenetriamine or cyclic amine, as illustrated below:

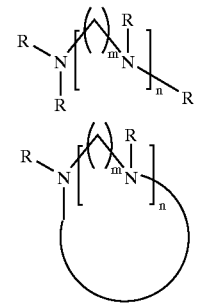

For the structures above, R is independently selected from the group consisting of hydrogen, $C_1$ to $C_{20}$ alkyl, cycloalkyl and aromatic groups which, optionally, contain heteroatoms. Furthermore, m is from 1 to 5, and n is from 0 to 5.

Specific examples of nitrogen-containing ligands include

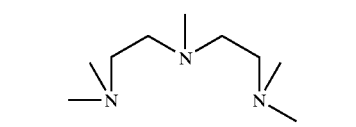

N,N,N',N'',N''-pentamethyldiethylenetriamine

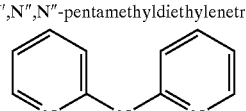

2,2'-dipyridylamine

-continued

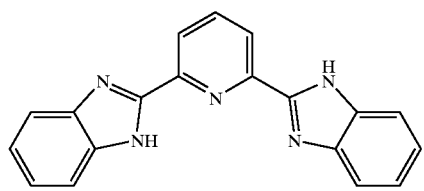

2,6-bis(1-hydrobenzimidazol-2-yl)pyridine

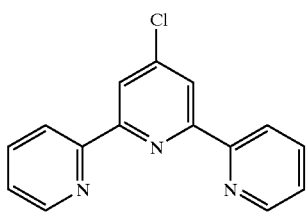

4-chloro-2,2′: 6′,2″-terpyridine

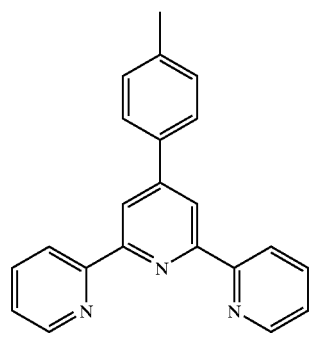

4′-(4-methylphenyl)-2,2′: 6′,2″-terpyridine

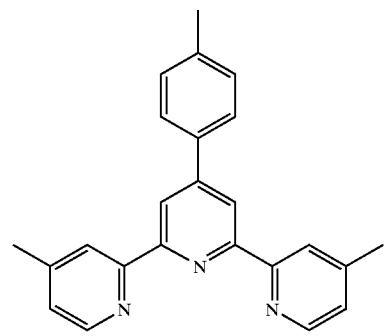

4-4′-dimethyl-4′-(4-methylphenyl)-2,2′: 6′,2″-terpyridine

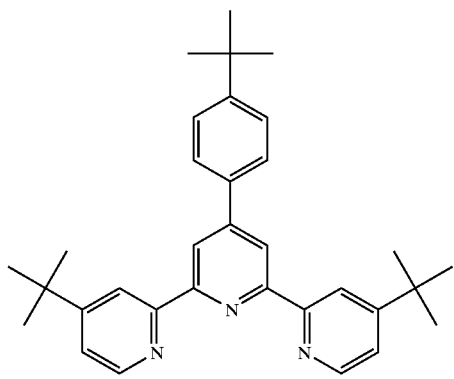

4-4′-4″-tri-tert-butyl-2,2′: 6′,2″-terpyridine

-continued

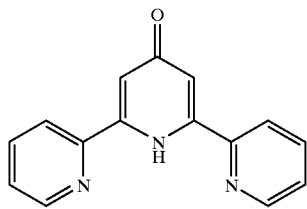

2,6-bis(2-pyridyl)-4(1H)-pyridone

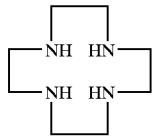

Cyclen(1,4,7,10-tetraazacyclododecane)

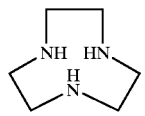

1,4,7,10-triazacyclononane

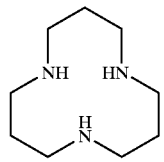

1,5,9-triazacyclododecane

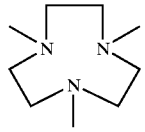

1,4,7,10-trimethyl-1,4,7-triazacyclononane

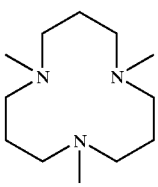

1,5,9-Trimethyl-1,5,9-triazacyclododecane

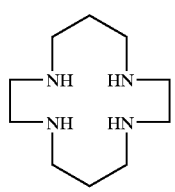

1,4,8,11-tetraazacyclotetradecane

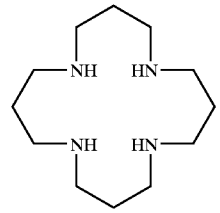

1,5,9,13-tetraazacyclohexadecane

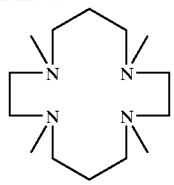

1,4,8,11-Tetramethyl-1,4,8,11-tetraazacyclotetradecane

In yet another preferred embodiment, L may be a pyrazolyl borate compound, as taught in U.S. Pat. No. 5,627,164 to Gorun, et al., incorporated by reference herein.

In a preferred embodiment, M is copper. Among the options for X, halogens are preferred. Suitable non-halide options for X include, but are not limited to, triflate, trifluoroacetate, perfluorotetraphenyl borate, tetrafluoro borate, hydride, alkyl groups or any other moiety into which a monomer can insert, such as an atom, or group of atoms, covalently or ionically bonded to M.

For each occurrence of Z, each Z is preferably independently selected from the group consisting of halogens, triflate, trifluoroacetate, perfluorotetraphenyl borate, tetrafluoro borate, hydride, alkyl, diethylether, tetrahydrofuran, acetonitrile, benzonitrile, dioxane, acetone, 2-butanone, phenylisocyanate, ethylene, carbon monoxide, 1-hexene and norbornene, or any other moiety into which a monomer can insert.

Advantageously, the catalysts of the present invention are not poisoned by compounds containing hydrocarbyl polar functional groups when used in the formation of polymers and copolymers synthesized all or in part from olefinic monomers. As such, the catalysts of the present invention are useful in preparing polymers and copolymers formed from olefinic monomers, such as polyethylene; polymers and copolymers formed from olefinic monomers containing hydrocarbyl polar functional groups, such as poly(methyl methacrylate); and copolymers derived from olefins and monomers containing hydrocarbyl polar functional groups, such as poly(ethylene-co-methyl methacrylate). One of skill in the art will know that the hydrocarbyl polar functional groups mentioned above include ethers, esters, ketones, alcohols, and carboxylic acids, among others.

Examples of the activating cocatalysts used above include, but are not limited to, aluminum compounds containing an Al—O bond, such as the alkylaluminoxanes, specifically methylaluminoxane ("MAO") and isobutyl modified methylaluminoxane; aluminum alkyls; aluminum halides; alkylaluminum halides; alkylaluminum alkoxides; alkylaluminum aryloxides; Lewis acids other than any of the foregoing list; and mixtures of the foregoing can also be used in conjunction with alkylating agents, such as dimethyl magnesium, methyl magnesium chloride and methyl lithium. Examples of such Lewis acids are those compounds corresponding to the formula: R""$_3$B, wherein R"", independently each occurrence, is selected from hydrogen, silyl, hydrocarbyl, halohydrocarbyl, alkoxide, aryloxide, amide or combinations thereof, said R"" having up to 30 non-hydrogen atoms.

It is to be appreciated by those skilled in the art that the above formula for the preferred Lewis acids represents an empirical formula, and that many Lewis acids exist as dimers or higher oligomers in solution or in the solid state. Other Lewis acids which are useful in the catalyst compositions of this invention will be apparent to those skilled in the art.

Other examples of such cocatalysts include salts of group 13 element complexes (new IUPAC notation). These and other examples of suitable cocatalysts and their use in organometallic polymerization are discussed in U.S. Pat. No. 5,198,401 and PCT patent documents WO 97/48736 and WO 96/40805, all incorporated by reference herein.

Preferred activating cocatalysts include trimethylaluminum, triisobutylaluminum, methylaluminoxane, ethylaluminoxane, chlorodiethyaluminum, dichloroethylaluminum, triethylboron, trimethylboron, triphenylboron and halogenated, especially fluorinated, triphenyl boron compounds.

The most highly preferred activating cocatalysts include, but are not limited to, triethylaluminum, methylaluminoxane, fluoro-substituted tetra-aryl borates, such as triphenylmethyl[tetrakis(pentafluorophenyl)borate], sodium tetrakis(3,5-bis(trifluoromethyl)phenyl)borate, and dimethylanilinium[tetrakis(pentafluorophenyl)borate], and fluoro-substituted triarylboranes, such as tris(4-fluorophenyl)boron, tris(2,4-difluorophenyl)boron, tris(3,5-bis(trifluoromethyl)phenyl)boron, tris(pentafluorophenyl) boron, (pentafluorophenyl-diphenyl)boron, and bis (pentafluorophenyl)phenylboron. Such fluoro-substituted triarylboranes may be readily synthesized according to techniques such as those disclosed in Marks, et al., J. Am. Chem. Soc., 113, 3623–3625 (1991), which is herein incorporated by reference.

Furthermore, the equivalent ratio of metal to activating cocatalyst is preferably in a range from 1:0.5 to 1:10$^4$, more preferably from 1:0.75 to 1:10$^3$. In most polymerization reactions, the equivalent ratio of catalyst:polymerizable compound employed is from 10$^{-12}$:1 to 10$^{-1}$:1, more preferably from 10$^{-9}$:1 to 10$^{-4}$:1.

The catalyst can be utilized by forming the metal complex LMXZ$_n$, as defined above, and, where required, combining the activating cocatalyst with the metal complex in a diluent. Optionally, an oxidizing agent may also be utilized in conjunction with the cocatalyst. Oxidizing agents may include, but are not limited to, NOBF$_4$, 1,4-benzoquinone, tetrachloro-1,4-benzoquinone, AgClO$_4$, Ag(C$_6$F$_5$)$_4$B, ferricinium (C$_6$F$_5$)$_4$B, (3,5-(CF$_3$)$_2$—(C$_6$H$_4$)B)Cp$_2$Fe$^+$, and (3,5-(CF$_3$)$_2$—(C$_6$H$_4$)B)Cp*$_2$Fe$^+$. The preparation may be conducted in the presence of one or more polymerizable monomers, if desired. Preferably, the catalysts are prepared at a temperature within the range from −100° C. to 300° C., preferably from 0° C. to 250° C., and most preferably from 0° C. to 100° C. Suitable solvents include liquid or supercritical gases, such as CO$_2$; straight- and branched-chain hydrocarbons, such as isobutane, butane, pentane, hexane, heptane, octane, and mixtures thereof; cyclic and acyclic hydrocarbons, such as cyclohexane, cycloheptane, methylcyclohexane and methylcycloheptane; halogenated hydrocarbons, such as chlorobenzene, dichlorobenzene, and perfluorinated C$_{2-10}$ alkanes; and aromatic and alkyl-substituted aromatic compounds, such as benzene, toluene and xylene. Suitable solvents also include liquid olefins which may act as monomers or comonomers, including ethylene, propylene, butadiene, 1-hexene, 3-methyl-1-pentene, 4-methyl-1-pentene, 1-octene, 1-decene, and 4-vinylcylohexane (including all isomers alone or in mixtures). Other solvents include anisole, methyl chloride, methylene chloride, chloroform, 2-pyrrolidone and N-methylpyrrolidone. Preferred solvents are aliphatic hydrocarbons and aromatic hydrocarbons, such as toluene.

Olefinic monomers useful in forming homopolymers and copolymers with the catalyst of the invention include, but are not limited to: (a) aliphatic olefins; (b) olefins having a hydrocarbyl polar functionality; and (c) mixtures of (i) at least one olefin having a hydrocarbyl polar functional group and (ii) at least one aliphatic olefin. Olefinic monomers include ethylenically unsaturated monomers, nonconjugated dienes, oligomers, and higher molecular weight, vinyl-terminated macromers. Examples include $C_{2-20}$ olefins, vinylcyclohexane, tetrafluoroethylene, and mixtures thereof. Preferred monomers include the $C_{2-10}$ α-olefins, especially ethylene, propylene, isobutylene, 1-butene, 1-hexene, 4-methyl-1-pentene, and 1-octene or mixtures of the same.

Monomers having hydrocarbyl polar functional groups useful in forming homopolymers and copolymers with the catalyst of the invention are vinyl ether and $C_1$ to $C_{20}$ alkyl vinyl ethers, such as n-butyl vinyl ether; acrylates, such as $C_1$ to $C_{24}$ alkyl acrylates, preferably t-butyl acrylate and lauryl acrylate; and methacrylates, such as methyl methacrylate.

In another embodiment, the invention provides one method for polymerizing olefinic monomers selected from the aforementioned group. The method of this embodiment comprises contacting the olefinic monomers under polymerization conditions with an activated catalyst compound comprising the reaction product of (a) a metal complex having the formula $LMXZ_n$, as defined above; and (b) an activating cocatalyst. Furthermore, by controlling the temperature, catalyst loading, ligand structure and residence time, product selectivity can be adjusted to produce individual polymers and copolymers with high selectivity.

A further embodiment comprises a method for polymerizing the aforementioned olefinic monomers in situ. This method includes contacting in situ under polymerization conditions compound $MXZ_n$, compound L, an activating cocatalyst, and one or more of the olefinic monomers. In this situation, the equivalent ratio of compound L to compound $MXZ_n$ is preferably from 0.25:1 to 4:1, and more preferably from 0.5:1 to 2:1.

In general, the polymerization may be accomplished at conditions well known in the art for Ziegler-Natta or Kaminsky-Sinn type polymerization reactions, that is, temperatures from −100° C. to 250° C., preferably from 0° C. to 250° C., and pressures from atmospheric to 2000 atmospheres (200 Mpa). Suitable polymerization conditions include those known to be useful for metallocene catalysts when activated by aluminum or boron compounds. Suspension, solution, slurry, gas phase or other process conditions may be employed, if desired. The catalysts may be supported, and such supported catalysts may be employed in the polymerizations of this invention. Preferred supports include alumina, silica, polymeric supports and meso-porous materials.

The polymerization typically will be conducted in the presence of a solvent. Suitable solvents include those previously described as useful in the preparation of the catalyst. Indeed, the polymerization may be conducted in the same solvent used in preparing the catalyst. Optionally, of course, the catalyst may be separately prepared in one solvent and used in another.

The polymerization will be conducted for a time sufficient to form the polymer, and the polymer is recovered by techniques well known in the art and illustrated in the following non-limiting examples which help to further described the invention.

EXAMPLES

Example 1

Synthesis of (2,6-Bis-[1-(2,6-dimethylphenylimino) ethyl]-pyridine)CuCl$_2$ ("I")

A 93 mg (0.56 mmol) quantity of CuCl$_2$•(H$_2$O)$_2$ mg, was dissolved in 10 mL anhydrous acetonitrile in a 100 mL Schlenk flask equipped with a stirbar and reflux condenser. Then, 2 mL of triethyl orthoformate was added and the clear green solution was heated to 84° C. Next, 202 mg (0.56 mmol) of 2,6-bis-[1-(2,6-dimethylphenylimino)ethyl]-pyridine was dissolved in a mixture of 10 mL anhydrous acetonitrile and 0.6 mL toluene at 70° C. and added to the copper chloride solution through the top of the condenser. The solution slowly became brown and, after 1 minute, a brown precipitate began to form. The mixture was stirred at 84° C. for an additional 20 minutes and cooled to room temperature. The brown precipitate was collected by filtration, rinsed with additional acetonitrile, and dried under vacuum (90 mg, 32% yield, FW 504.0 g/mol). IR (KBr): 3400 (w, residual O—H), 3080 (m), 2945 (m), 2909 (m), 1618 (m, Cu—Cl), 1565 (C=N), 1470 (s), 1373 (m), 1265 (s), 1223 (s), 1101 (w), 1034 (m), 814 (m), 770 (m), 744 (sh) cm$^{-1}$.

Example 2

Preparation of (2,6-Bis-[1-(2,6-dimethylphenylimino)ethyl]-pyridine)CuCl ("II").

A 67 mg (0.0.68 mmol) quantity of CuCl (rinsed with aqueous HCl and dried) was slurried in 20 mL anhydrous THF in a Schlenk flask equipped with a stirbar and reflux condenser under argon. Next, 2 mL of triethyl orthoformate was added and the slurry was heated to 60° C. The 2,6-bis-[1-(2,6-dimethylimino)ethyl]-pyridine (250 mg, 0.0.68 mmol) was dissolved in anhydrous THF and cannulated into the warm slurry. The CuCl began to dissolve and the mixture was allowed to reflux under argon for several hours, after which it had assumed a dark brown color. The solvent was removed by cannula and the remaining solids rinsed with a small amount of anhydrous acetonitrile and dried under vacuum. Approximately 50 mg (16% yield, FW 468.5 g/mol) was recovered in the drybox as a brown powder. NMR (d$_3$-acetonitrile): δ 8.29 (app. d, 2H, Py-m), 8.27 (app. t,1H, Py-p), 7.14 (d, J=7.6 Hz, 4H, aniline m), 7.02 (t, J=7.4 Hz, 2H, aniline p), 2.27 (s, 6H, N=CMe), 2.05 (s, 12H, aniline Me). IR (KBr): 3450 (w), 3063 (w), 3017 (w), 2972 (m), 2917 (m), 1928 (w), 1620 (m), 1588 (s), 1468 (vs), 1368 (m), 1250 (s), 1206 (s), 1092 (m), 1036 (w), 988 (w), 810 (m), 770 (s) cm$^{-1}$.

Example 3

Preparation of (N,N,N',N'',N''-Pentamethyldiethylenetriamine)CuCl$_2$ ("III").

An 8.12 g (0.0952 mol) quantity of CuCl$_2$•(H$_2$O)$_2$ was dissolved in 250 mL ethanol in a 500 mL flask equipped with a stirbar and reflux condenser. Then, 50 mL of diethylene orthoformate was added, and the solution was stirred for 15 minutes. Next, a 7.5 g (FW 173.30, 0.0866 mol) quantity of N,N,N',N'',N''-pentamethyldiethylenetriamine was added. The mixture was refluxed for 30 minutes and cooled to room temperature. The flask was sealed and cooled in a refrigerator for crystallization to occur. The blue crystals were collected by filtration, rinsed with additional ethanol, and dried under a vacuum resulting in 2.13 g of the complex.

Example 4

Ethylene Polymerization

In an argon glovebox, 1.416 g of a 30 wt % methylaluminoxane solution in toluene (Albemarle, stored at −35° C., 425 mg MAO, 7.32 mmol) was weighed into a soap-washed and oven-dried 300 mL Parr glass liner. Then, 25 mL of chlorobenzene (distilled from $CaH_2$) and 25 mL of toluene (dried by passage over alumina and Q5 copper catalyst) were added followed by 45.6 mg (0.090 mmol) of I, the copper complex formed in Example 1. The liner was then placed into a 300 mL Hasteloy Parr reactor (soap-washed and oven-dried), which was quickly assembled, sealed and removed from the glove box. The reactor was heated to. 80° C. and the contents were stirred at approximately 350 rpm with an air-driven stirring shaft. After a quick nitrogen purge of the connected lines, the reactor was pressurized to 600 psi with ethylene (passed through drying columns of molecular sieves and Q5 copper catalyst). The reactor was sealed off from all gas lines and stirred at 80° C. overnight, after which it was cooled to room temperature and vented. The contents were poured into a large excess (approx. 1 L) of 5% HCl in methanol. The white insoluble polymer was collected by filtration, rinsed with a small volume of additional methanol, and dried in a vacuum oven overnight at 75° C. to yield 112 mg of the polymer. IR (KBr): 2917 (s), 2851 (s), 1472 (m), 729 (w), 719 (w) $cm^{-1}$. Melting point (DSC, $2^{nd}$ heat): 134.9° C.

Example 5

Polymerization of Ethylene

In an argon glovebox, 0.357 g of a 30 wt % methylaluminoxane solution in toluene (Albemarle, stored at −35° C., 107 mg MAO, 1.84 mmol) was weighed into a soap-washed and oven-dried 300 mL Hasteloy Parr reactor. Then, 100 mL of toluene (dried by passage over alumina and Q5 copper catalyst) was added followed by 45.6 mg (0.090 mmol) of I, the copper complex formed in Example 1. The reactor was quickly assembled, sealed, removed from the glove box, and heated to 80° C., and its contents were stirred at approximately 350 rpm with an air-driven stirring shaft. After a quick nitrogen purge of the connected lines, the reactor was pressurized to 600 psi with ethylene (passed through drying columns of molecular sieves and Q5 copper catalyst). The reactor was sealed off from all gas lines and stirred for two days at 80° C., after which it was cooled to room temperature and vented. The contents were poured into a large excess (approx. 1 L) of 5% HCl in methanol. The white insoluble polymer was collected by filtration, rinsed with a small volume of additional methanol, and dried in a vacuum oven overnight at 75° C. to yield 226 mg of the polymer.

Example 6

Polymerization of Ethylene

In an argon glovebox, 0.354 g of a 30 wt % methylaluminoxane solution in toluene (Albemarle, stored at −35° C., 106 mg MAO, 1.83 mmol) was weighed into a soap-washed and oven-dried 300 mL Parr glass liner. Next, 25mL of chlorobenzene (distilled from $CaH_2$) and 25 mL of toluene (dried by passage over alumina and Q5 copper catalyst) were added, followed by 45.6 mg (0.090 mmol) of I, the copper complex from Example 1. The liner was placed into a 300 mL Hasteloy Parr reactor (soap-washed and oven-dried), which was quickly assembled, sealed and removed from the glove box. The reactor was heated to 80° C. and the contents were stirred at ca. 350 rpm with an air-driven stirring shaft. After a quick nitrogen purge of the connected lines, the reactor was pressurized to 600 psi with ethylene (passed through drying columns of molecular sieves and Q5 copper catalyst). The reactor was sealed off from all gas lines and stirred overnight at 80° C., after which it was cooled to room temperature and vented. The contents were poured into a large excess (approx. 1 L) of 5% HCl in methanol. The white insoluble polymer was collected by filtration, rinsed with a small volume of additional methanol, and dried in a vacuum oven overnight at 75° C. to yield 91 mg of the polymer.

Example 7

Polymerization of Ethylene

A glass-lined Parr reactor was loaded in an argon glove box with 100 mL of toluene and 10.53 g of 30 wt % MAO solution in toluene, and 0.0112 g of III, the copper complex formed in Example 3, was added. The Parr reactor was then sealed, placed in a fume hood and pressurized with 750 psig ethylene at 60° C. for 24 hours. The reactor was cooled, vented and its contents poured into a solution of MeOH/HCl (300 mL MeOH/100 mL 10% HCl). The mixture was stirred for 24 hours to remove catalyst residues. The polymer was isolated by filtration and dried under vacuum at 60° C. for 24 hours. The yield of the polyethylene was 120 mg. The IR spectrum (film) of the product showed the characteristic linear crystalline polyethylene doublet absorption at 719 and 729 $cm^{-1}$.

Example 8

Polymerization of n-Butyl Acrylate

In an argon glovebox, a 30 mL septum bottle was loaded with a 0.01 g (FW 309.75, 0.0322 mmol) quantity of III, the copper complex formed in Example 3, and 15 mL of toluene. A 0.77 g quantity of 30 wt % MAO solution in toluene was then added. The yellow solution turned colorless upon the MAO addition. Then, 5 g (FW 128.17, 0.039 mol) of n-butyl acrylate was added. The bottle was sealed in the glovebox and placed into a fume hood. The solution was stirred for 72 hours at 25° C. The viscous solution was added to a solution of MeOH/HCl (300 mL MeOH/100 mL 10% HCl solution to precipitate the polymer. The product was washed with water, then methanol, and dried in vacuum oven for 24 hours at 60° C. The yield of the poly(n-butyl acrylate) was 3.26 g. The IR spectrum (film) of the product showed the characteristic polymer ester absorption peak at 1736 $cm^{-1}$. On polymerization, the monomeric ester absorption peak shifts from 1728 $cm^{-1}$ to the polymeric ester absorption at 1736 $cm^{-1}$. The characteristic double bond absorption peaks at 1637 and 812 $cm^{-1}$ also disappear on polymerization. The GPC data (solvent: THF, polystyrene standard) gave a $M_n$ of 119,600 and a $M_w$ of 204,780. $^{13}C$ NMR (ppm, $CDCl_3$): 13.7 [s, —$CH_2$—CH(COOCH$_2$CH$_2$CH$_2$$\underline{C}$H$_3$)-], 19.1 [s, —$CH_2$—CH (COOCH$_2$CH$_2$$\underline{C}$H$_2$CH$_3$)-], 30.7 [s, —$CH_2$—CH(COOCH$_2$$\underline{C}$H$_2$CH$_2$CH$_3$)-], 34–37 [m, —$\underline{C}$H$_2$CH(COOCH$_2$ CH$_2$ CH$_2$CH$_3$)-], 41–42 [m, —CH$_2$—$\underline{C}$H(COOCH$_2$CH$_2$CH$_2$CH$_3$)-],64.5 [s, —CH$_2$—CH(COO $\underline{C}$H$_2$CH$_2$CH$_2$CH$_3$)-], 174–175 [m, —CH$_2$—CH( $\underline{C}$OOCH$_2$CH$_2$CH$_2$CH$_3$)-]. There were no resonances due to olefin from the monomer.

Example 9

Copolymerization of Ethylene and t-Butyl Acrylate

A glass-lined Parr reactor was loaded in an argon glove box with 100 mL of toluene and 10.53 g of 30 wt % MAO solution in toluene. Then, a 0.0112 g quantity of III, the complex formed in Example 3, was added followed by 5 g of tert-butyl acrylate. The Parr reactor was sealed, placed in a fume hood and pressurized with 350 psig ethylene and heated to 60° C. with stirring. The ethylene pressure was then increased to 700 psig and the reactor continued to stir for 18 hours at 60° C. The reactor was cooled, vented and its contents poured into a solution of MeOH/HCl (300 mL MeOH/100 mL 10% HCl). The mixture was stirred for 24 hours to remove catalyst residues. The polymer was isolated by filtration and dried under vacuum at 60° C. for 24 hours. The yield of the copolymer was 310 mg. The IR spectrum of the product showed the characteristic ester absorption peak at 1728 $cm^{-1}$.

Example 10

Polymerization of Ethylene

In an argon glove box, a glass-lined Parr reactor was loaded with 120 mL of toluene and 2.84 g of 30 wt % MAO solution in toluene. A 10.6 mg quantity of $CuCl_2.2H_2O$ (FW 170.48, $6.218\times10^{-2}$ mmol) was then added (Al/Cu ratio of 234) followed by a 10.4 mg quantity of N,N,N',N'',N''-pentamethyldiethylenetriamine (FW 173.30, $6.00\times10^{-2}$ mmol) ligand. The Parr reactor was sealed, placed in a fume hood and pressurized with 750 psig ethylene, and polymerized at 60° C. for 20 hours. The reactor was cooled, vented and quenched with methanol. The polymer was soaked in a MeOH/HCl (300 mL MeOH/100 mL 10% HCl) mixture for 24 hours to remove catalyst residues. The polymer was isolated by filtration and dried under vacuum at 60° C. for 24 hours. The yield of the polyethylene was 50 mg. The IR spectrum (film) of the product showed the characteristic linear crystalline polyethylene doublet absorption at 719 and 729 $cm^{-1}$.

Example 11

Polymerization of t-Butyl Acrylate

In an argon glovebox, a 30 mL septum bottle was loaded with a 0.0031 g quantity of $CuCl_2.2H_2O$ (FW 170.48, 0.02 mmol) and 15 mL of toluene. A 0.00315 g quantity of N,N,N',N'',N''-pentamethyldiethylenetriamine ligand was then added, resulting in the formation of a yellow solution. Next, a 0.88 g quantity of 30 wt % MAO solution in toluene was added. The yellow solution turned colorless upon MAO addition. Then, 5 g of t-butyl acrylate (FW 128.17, 0.039 mol) was added. The bottle was sealed in the glove box and placed in a fume hood. The solution was heated at 60° C. for 3 hours. The viscous solution was cooled to room temperature and was added to a MeOH/HCl (300 mL MeOH/100 mL 10% HCl) solution to precipitate the polymer. The product was washed with water, then methanol, and dried in vacuum oven at 60° C. for 24 hours. The yield of the poly(t-butyl acrylate) was 400 mg. The IR spectrum (film) of the product showed the characteristic ester peak at 1734 $cm^{-1}$. $^{13}C$ NMR (ppm, $CDCl_3$): 27.7 (s, —$CH_2$—CH(COOC($\underline{C}H_3$)$_3$—), 35.9 and 37.1 (m, —$\underline{C}H_2$—CH(COOC($CH_3$)$_3$), 42.3 (m, —$CH_2$—$\underline{C}H$(COOC($CH_3$)$_3$—), 79.6 (s, —$CH_2$—CH(COO$\underline{C}$($CH_3$)$_3$—), 173.3 (s, —$CH_2$—CH($\underline{C}$OOC($CH_3$)$_3$—). There were no resonances due to olefin from the monomer.

Example 12

Copolymerization of Ethylene and t-Butyl Acrylate

In an argon glove box, a 0.0062 g quantity of $CuCl_2.2H_2O$ (FW 170.48, 0.04 mmol) and 100 mL of toluene were loaded into a glass-lined Parr reactor. Then, a 0.0068 g quantity of N,N,N',N'',N''-pentamethyldiethylenetriamine ligand was added, which cause the solution to turn yellow. Next, a 1.53 g quantity of 30 wt % MAO solution in toluene was added. Then, a 5 g quantity of t-butyl acrylate (FW 128.17, 0.039 mol) was added. The Parr reactor was then sealed, placed in a fume hood, and pressurized with 750 psig ethylene, and polymerized at 60° C. for 20 hours. The reactor was cooled, vented and quenched with methanol. The polymer was soaked in a MeOH/HCl mixture (300 mL MeOH/100 mL 10% HCl) for 24 hours to remove catalyst residues. The polymer was isolated by filtration and dried under vacuum at 60° C. for 24 hours. The yield of the product was 250 mg. $^{13}C$ NMR spectra of the product showed EAE, EAA/AAE and AAA triads and a copolymer composition of 56% ethylene (E) and 46% acrylate (A).

Example 13

Polymerization of Ethylene

A glass-lined Parr reactor was loaded in an argon glove box with 120 mL of toluene and 2.84 g of a 30 wt % MAO solution in toluene. A 11.0 mg quantity of $CuCl_2.2H_2O$ (FW 170.48, $6.452\times10^{-2}$ mmol) was then added (Al:Cu ratio of 227:1) followed by a 10.0 mg quantity of 1,4,7-trimethyl-1,4,7-triazacyclononane (FW 171.29, $5.84\times10^{-2}$ mmol) ligand. The Parr reactor was then sealed, placed in a fume hood, and pressurized with 750 psig ethylene, and polymerized at 60° C. for 16 hours. The reactor was cooled, vented and quenched with methanol. The polymer was soaked in a MeOH/HCl mixture (300 mL MeOH/100 mL 10% HCl) for 24 hours to remove catalyst residues. The polymer was isolated by filtration and dried under vacuum at 60° C. for 24 hours. The yield of the polyethylene was 110 mg. The IR spectrum (film) of the product showed the characteristic linear crystalline polyethylene doublet absorption at 719 and 729 $cm^{-1}$.

Example 14

Polymerization of n-Butyl Acrylate

In an argon glovebox, a 30 mL septum bottle was loaded with a 0.0061 g quantity of $CuCl_2.2H_2O$ (FW 170.98, $3.57\times10^{-2}$ mmol) and 15 mL of toluene. Then, a 0.0056 g quantity of 1,4,7-trimethyl-1,4,7-triazacyclononane (FW 171.29, $3.327\times10^{-2}$ mmol) ligand was added, resulting in a yellow solution. A 0.77 g quantity of 30 wt % MAO solution in toluene was then added. The yellow solution turned colorless upon MAO addition. Next, a 5 g quantity of n-butyl acrylate (FW 128.17, 0.039 mol) was added. The bottle was sealed in the glove box and placed in a fume hood. The solution was stirred at 25° C. for 72 hours. The viscous solution was added to a MeOH/HCl (300 mL MeOH/100 mL 10% HCl) solution to precipitate the polymer. The product was washed with water, then methanol, and dried in a vacuum oven at 60° C. for 24 hours. The yield of the poly(n-butyl acrylate) was 4.12 g. The IR spectrum (film) of the product showed the characteristic polymer ester absorption peak at 1736 $cm^{-1}$. After polymerization, the monomeric ester absorption peak shifted from 1728 $cm^{-1}$ to the polymeric ester absorption at 1736 $cm^{-1}$. The characteristic double bond absorption peaks at 1637 $cm^{-1}$ and 812 $cm^{-1}$ also disappeared upon polymerization. The GPC data (solvent: THF, polystyrene standard) gave a $M_n$ of 112,200 and a $M_w$ of 160,700. $^{13}C$ NMR (ppm,$CDCl_3$): 13.6 [s, —$CH_2$—CH(COOC$H_2$C$H_2$C$H_3$)-], 19.1 [s, —$CH_2$—CH (COOC$H_2$C$H_2$$\underline{C}H_2$C$H_3$)-], 30.7 [s, —$CH_2$—CH (COOC$H_2$$\underline{C}H_2$C$H_2$C$H_3$)-], 34–37 [m, —$\underline{C}H_2$CH(COOC$H_2$ C$H_2$ C$H_2$C$H_3$)-], 41–42 [m, —C$H_2$—

CH(COOCH$_2$CH$_2$CH$_2$CH$_3$)-], 64.5 [s, —CH$_2$—CH(COO CH$_2$CH$_2$CH$_2$CH$_3$)-],174–175 [m, —CH$_2$—CH( COOCH$_2$CH$_2$CH$_2$CH$_3$)-]. There were no resonances due to olefin from the monomer.

Example 15

Polymerization of n-Butyl Acrylate

In an argon glovebox, a 30 mL septum bottle was loaded with a 0.0061 g quantity of CuCl$_2$.2H$_2$O(FW 170.98, 0.0357 mmol) and 15 mL of toluene. Then, a 0.0130 g quantity of 4.4',4"-tri-tert-butyl-2,2':6',2"-terpyridine (FW 401.60, 0.0324 mmol) ligand was added resulting in the formation of a yellow solution. A 0.77 g quantity of 30 wt % MAO solution in toluene was then added. The yellow solution turned colorless upon MAO addition. Next, 5 g of n-butyl acrylate (FW. 128.17, 0.039 mol) was added. The bottle was sealed in the glove box and placed in a fume hood. The solution was stirred at 25° C. for 72 hours. The viscous solution was added to a MeOH/HCl (300 mL MeOH/100 mL 10% HCl) solution to precipitate the polymer. The product was washed with water, then methanol, and dried in vacuum oven at 60° C. for 24 hours. The yield of the poly(n-butyl acrylate) was 3.12 g. The IR spectrum (film) of the product showed the characteristic polymer ester absorption peak at 1736 cm$^{-1}$. On polymerization, the monomeric ester absorption peak shifted from 1728 cm$^{-1}$ to the polymeric ester absorption at 1736 cm$^{-1}$. The characteristic double bond absorption peaks at 1637 cm$^{-1}$ and 812 cm$^{-1}$ also disappeared upon polymerization. The GPC data (solvent: THF, polystyrene standard) gave a M$_n$ of 124,100 and a M$_w$ of 214,600 $^{13}$C NMR (ppm,CDCl$_3$): 13.7 [s, —CH$_2$—CH (COOCH$_2$CH$_2$CH$_2$CH$_3$)-], 19.1 [s, —CH$_2$—CH (COOCH$_2$CH$_2$CH$_2$CH$_3$], 30.7 [s, —CH$_2$—CH(COOCH$_2$ CH$_2$CH$_2$CH$_3$)-], 34–37[m, —CH$_2$CH(COOCH$_2$ CH$_2$ CH$_2$ CH$_3$)], 41–42 [m, —CH$_2$— CH(COOCH$_2$CH$_2$CH$_2$CH$_3$)-], 64.5 [s, —CH$_2$—CH(COO CH$_2$CH$_2$CH$_2$CH$_3$)-], 174–175 [m, —CH$_2$—CH( COOCHH$_2$CH$_2$CH$_2$CH$_3$)-]. There were no resonances due to olefin from the monomer.

The foregoing examples clearly demonstrate that the novel composition of the instant invention can be used as an effective polymerization catalyst to make polymers and copolymers, including copolymers having polar functionality. More specifically, the examples show how polar monomers can be readily polymerized without poisoning the catalyst. Also, the chain, as opposed to the branches, contains a significant quantity of the polar monomers. Furthermore, the polymers formed are not highly branched. Additionally, the examples show that the polymers formed have a high percent of polar monomer content (e.g., greater than about 15 mol %). Finally, there are a variety of polar monomers which may be incorporated into the olefinic polymer and copolymer products. These features overcome the disadvantages of most organometallic catalyst technology used today, as discussed above in the background section.

What is claimed is:

1. A method for polymerizing olefinic monomers, comprising contacting the following compounds in situ:
   (a) a metal compound MXZ$_n$, wherein:
      (i) M is selected from the group consisting of Cu, Ag and Au,
      (ii) X is selected from the group consisting of halide, hydride, triflate, acetate, borate, C$_1$ through C$_{12}$ alkyl, C$_1$ through C$_{12}$ alkoxy, C$_3$ through C$_{12}$ cycloalkyl, C$_3$ through C$_{12}$ cycloalkoxy, aryl, thiolate, nitrate, sulfate, nitrile, and hydroxide, and
      (iii) Z is selected from the group consisting of diethylether, tetrahydrofuran, dioxane, acetone, 2 butanone, phenylisocyanate, halide, hydride, triflate, acetate, borate, C$_1$ through C$_{12}$ alkyl, C$_1$ through C$_{12}$ alkoxy, C$_3$ through C$_{12}$ cycloalkyl, C$_3$ through C$_{12}$ cycloalkoxy, aryl, thiolate, carbon monoxide, nitrate, nitrile, hydroxide, sulfate, olefins, and water, wherein n equals 0, 1 or 2;
   (b) a compound L comprising a tri-dentate nitrogen-containing ligand selected from the group consisting of 2,2':6',2"-terpyridine, [2,6-bis(1-phenylimino) ethyl]pyridine, 1,4,7-triazacyclononane, and their substituted derivatives;
   (c) an activating cocatalyst; and
   (d) one or more olefinic monomers selected from the group consisting of:
      (i) aliphatic olefins,
      (ii) olefins having a hydrocarbyl polar functional group and
      (iii) mixtures of at least one olefin having a hydrocarbyl polar functional group and at least one aliphatic olefin.

2. The method according to claim 1 wherein M is Cu.

3. The method according to claim 1 wherein for each occurrence of Z, each Z is independently selected from the group consisting of diethylether, tetrahydrofuran, acetonitrile, benzonitrile, dioxane, acetone, 2-butanone, phenylisocyanate, ethylene, carbon monoxide, 1-hexene and norbornene.

4. The method of claim 1 wherein the activating cocatalyst is selected from the group consisting of alkylaluminoxanes, aluminum alkyls, aluminum halides, alkyl aluminum halides, Lewis acids other than any of the foregoing, alkylating agents, and mixtures thereof.

5. The method of claim 4 wherein the activating cocatalyst is methylaluminoxane.

6. The method of claim 1 wherein the contacting step is performed at a temperature range of from about –100° C. to about 250° C. and at a pressure range of from about 15 psig to about 30,000 psig.

7. The method of claim 1 wherein the contacting step is conducted in a solvent.

8. The method of claim 7 wherein the solvent is selected from the group consisting of an aliphatic hydrocarbon solvent, an aromatic hydrocarbon solvent, a halogenated aromatic solvent, and mixtures thereof.

9. The method of claim 1 wherein said olefinic monomers are selected from the group consisting of acyclic aliphatic olefins and olefins having a hydrocarbyl polar functional group wherein a homopolymer is formed.

10. The method of claim 1 wherein said olefinic monomers are selected from mixtures of at least one olefin having a hydrocarbyl polar functional group and at least one acyclic aliphatic olefin, wherein a copolymer is formed.

11. The method of claim 1 wherein said olefinic monomers are ethylene, propylene and 1-butene.

12. The method of claim 1 wherein said olefinic monomers are n-butyl acrylate and 1-butyl acrylate.

13. The method of claim 1 wherein said olefinic monomers are ethylene and n-butyl acrylate.

14. The method of claim 1 wherein said olefinic monomers are ethylene and t-butyl acrylate.

15. A method for polymerizing olefinic monomers, comprising the steps of:
   (a) forming an activated catalyst compound by contacting a metal complex having the formula LMXZ$_n$ with an activating cocatalyst, wherein M is selected from the group consisting of Cu, Ag and Au; X is selected from the group consisting of halide, hydride, triflate, acetate, borate, $C_1$ through $C_{12}$ alkyl, $C_1$ through $C_{12}$ alkoxy, $C_3$ through $C_{12}$ cycloalkyl, $C_3$ through $C_{12}$ cycloalkoxy, aryl, thiolate, nitrate, sulfate, nitrile, and hydroxide Z is selected from the group consisting of diethylether, tetrahydrofuran, dioxane, acetone, 2-butanone, phenylisocyanate, halide, hydride, triflate, acetate, borate, $C_1$, through $C_{12}$ alkyl, $C_1$ through $C_{12}$ alkoxy, $C_3$ through $C_{12}$ cycloalkyl, $C_3$ through $C_{12}$ cycloalkoxy, aryl, thiolate, carbon monoxide, nitrate, nitrile, hydroxide, sulfate, olefins, and water n equals 0, 1 or 2; and L is a tri-dentate nitrogen-containing ligand selected from the group consisting of 2,2':6',2"-terpyridine, [2,6-bis(1-phenylimino)ethyl]pyridine, 1,4,7-triazacyclononane, and their substituted derivatives; and (b) contacting the activated catalyst compound with one or more olefinic monomers selected from the group consisting of:
 (i) aliphatic olefins,
 (ii) olefins having a hydrocarbyl polar functional group and
 (iii) mixtures of at least one olefin having a hydrocarbyl polar functional group and at least one aliphatic olefin.

16. The method according to claim 15 wherein M is Cu.

17. The method according to claim 15 wherein for each occurrence of Z, each Z is independently selected from the group consisting of diethylether, tetrahydrofuran, acetonitrile, benzonitrile, dioxane, acetone, 2-butanone, phenylisocyanate, ethylene, carbon monoxide, 1-hexene and norbornene.

18. The method according to claim 15 wherein the activating cocatalyst is selected from the group consisting of alkylaluminoxanes, aluminum alkyls, aluminum halides, alkyl aluminum halides, Lewis acids other than any of the foregoing, alkylating agents, and mixtures thereof.

19. The method according to claim 18 wherein the activating cocatalyst is methylaluminoxane.

20. The method of claim 15 wherein the steps are performed at a temperature range of from about −100° C. to about 250° C. and at a pressure range of from about 15 psig to about 30,000 psig.

21. The method of claim 15 wherein the contacting step b is conducted in a solvent.

22. The method of claim 21 wherein the solvent is selected from the group consisting of an aliphatic hydrocarbon solvent, an aromatic hydrocarbon solvent, a halogenated aromatic solvent, and mixtures thereof.

23. The method of claim 15 wherein said olefinic monomers are selected from the group consisting of acyclic aliphatic olefins and olefins having a hydrocarbyl polar functional group wherein a homopolymer is formed.

24. The method of claim 15 wherein said olefinic monomers are selected from mixtures of at least one olefin having a hydrocarbyl polar functional group and at least one acyclic aliphatic olefin, wherein a copolymer is formed.

25. The method of claim 15 wherein said olefinic monomers are ethylene, propylene and 1-butene.

26. The method of claim 15 wherein said olefinic monomers are n-butyl acrylate and t-butyl acrylate.

27. The method of claim 15 wherein said olefinic monomers are ethylene and n-butyl acrylate.

28. The method of claim 15 wherein said olefinic monomers are ethylene and t-butyl acrylate.

* * * * *